(12) United States Patent
Bramanti et al.

(10) Patent No.: US 10,597,716 B2
(45) Date of Patent: Mar. 24, 2020

(54) DEVICE FOR NUCLEIC ACID SEQUENCING

(71) Applicant: STMICROELECTRONICS S.R.L., Agrate Brianza (IT)

(72) Inventors: Alessandro Paolo Bramanti, Maglie (IT); Marco Angelo Bianchessi, Melzo (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 470 days.

(21) Appl. No.: 15/394,371

(22) Filed: Dec. 29, 2016

(65) Prior Publication Data

US 2017/0369943 A1   Dec. 28, 2017

(30) Foreign Application Priority Data

Jun. 28, 2016  (IT) .................... 102016000067063

(51) Int. Cl.
*C12P 19/34*    (2006.01)
*C12Q 1/6874*   (2018.01)
*C12Q 1/6869*   (2018.01)

(52) U.S. Cl.
CPC ......... *C12Q 1/6874* (2013.01); *C12Q 1/6869* (2013.01)

(58) Field of Classification Search
None
See application file for complete search history.

(56) References Cited

U.S. PATENT DOCUMENTS

| | | | | |
|---|---|---|---|---|
| 2006/0177840 A1* | 8/2006 | Slater | ........................ | C07K 1/13 435/6.16 |
| 2007/0215472 A1* | 9/2007 | Slater | ............... | G01N 27/44765 204/451 |
| 2008/0227211 A1* | 9/2008 | Meagher | .............. | C12Q 1/6827 436/94 |
| 2008/0241950 A1 | 10/2008 | Meagher et al. | | |
| 2012/0202948 A1* | 8/2012 | Lin | ....................... | C07K 14/001 525/54.1 |
| 2015/0182966 A1* | 7/2015 | Coursey | .................... | B01L 7/52 435/3 |

OTHER PUBLICATIONS

Meagher et al., "Free-solution electrophoresis of DNA modified with drag-tags at both ends," *Electrophoresis* 27:1702-1712, 2006.
Meagher et al., "Sequencing of DNA by by Free-Solution Capillary Electrophoresis Using a Genetically Engineered Protein Polymer Drag-Tag," *Anal. Chem.*80(8):2842-2848, 2008.
Namiot et al., "DNA Sequencing Using Specific Long-Range Interaction between Macromolecules," *Biophysics* 57(6):716-721, 2012.
Won et al., "Protein polymer drag-tags for DNA separations by end-labeled free-solution electrophoresis," *Electrophoresis* 26:2138-2148, 2005.

* cited by examiner

*Primary Examiner* — Kenneth R Horlick
(74) *Attorney, Agent, or Firm* — Seed IP Law Group LLP (57) ABSTRACT

A method for sequencing a nucleic acid strand, comprising the steps of: providing a solution containing truncated strands having lengths different from one another terminating with a respective dideoxynucleotide from among ddATP, ddTTP, ddGTP, and ddCTP; functionalizing first masses by a donor molecule and second masses by an acceptor molecule such as to generate a light emission when they come into mutual contact; coupling a first mass to a first end of each truncated strand; coupling the second masses to a respective terminal dideoxynucleotide of each strand; applying an AC electrical field having variable frequencies that are such as to generate, on each second mass, a net movement directed towards the first mass; acquiring a plurality of light radiations for each frequency value; and associating each light radiation acquired to a respective dideoxynucleotide and, thus, to a respective nucleotide base.

20 Claims, 3 Drawing Sheets

DEVICE FOR NUCLEIC ACID SEQUENCING

BACKGROUND

Technical Field

The present disclosure relates to a method and a device for nucleic acid sequencing.

Description of the Related Art

Known in the art are methods for DNA sequencing. Sequencing is fundamental for characterizing a macromolecule, for example in order to determine the order of the amino acids of a protein or the sequence of bases of a nucleic acid. Sequencing of an entire genome may enable prediction of the sequence of all the proteins that this is potentially able to produce.

A method for DNA sequencing known in the prior art envisages the use of dideoxynucleotide terminators and is known as the "Sanger method". The Sanger method consists of three steps: preparation of the sample, sequencing reaction, and electrophoresis. In the first step of preparation of the sample, the DNA strand that is to be sequenced is subjected to PCR (Polymerase Chain Reaction) in order to amplify it, i.e., obtain a plurality of identical copies thereof. Other techniques such as recombinant DNA may also be used. In the second, sequencing reaction step, the biological sample is subjected to denaturing, primer annealing, copy of the strand, and termination. With denaturing, the DNA is separated into individual strands. During primer annealing, a primer is added to the end 3' of one of the two strands. The primer is synthesized artificially and appropriately for the DNA sequence to be sequenced.

Four mixtures are then prepared, one for each base, added to which is DNA polymerase (step of copy of the strand), the four nucleotides (dATP, dCTP, dGTP, dTTP), and an amount of a dideoxynucleotide triphosphate (ddNTP, for example, ddATP), i.e., a nucleotide without the —OH group in position 3' of the sugar.

The above may, however, be added by the DNA polymerase to a DNA strand being synthesized via formation of a phosphodiester bond between its 5'-phosphate and 3'-OH of the previous residue. However, since ddNTPs lack the —OH group in position 3', the subsequent nucleotide may not be bound as occurs in natural DNA replication. For this reason, the synthesis stops at the position in which a ddNTP has been incorporated at the growing end of a DNA strand (termination step).

The new strands, each of which terminates with a ddNTP, for instance a ddATP in the example considered, have lengths that are different from one another. Once DNA polymerase encounters a T base on the template strand, it may add a dATP or a ddATP. If a dATP is added, growth of the strand continues, whereas if a ddATP is added, growth of the strand stops. This process is carried out for all four nucleotides.

Then, the strands thus synthesized are denatured and separated from the template strands. At this point, the preparation is ready for the electrophoresis step.

Electrophoresis is an electrokinetic process in which charged molecules and particles, under the influence of an electrical field, migrate in the direction of a pole that has opposite charge from that of the charged molecules. Owing to the presence of the phosphate groups, the DNA molecules are negatively charged and will thus migrate towards the positive pole (anode) if subjected to an electrical field, with a rate that depends also upon their length, as well as upon the field intensity.

Introduction of capillary electrophoresis for separation of marked fragments has enabled a considerable increase in the processing rate. There have further been developed automatic sequencers that are able to carry out multiple electrophoretic runs.

However, the use of the electrophoresis technique renders the Sanger method impractical to integrate in a portable biomedical device such as one that is obtained using MEMS technology.

New-generation sequencers, which are not based upon the Sanger method, use in-vitro amplification techniques and an array system for simultaneous sequencing of millions of DNA fragments. These improvements have enabled new platforms to reduce drastically the times and costs involved even though they require a demanding post-processing step and present limits of precision above all in counting the occurrences of repeated sequences. Further, these techniques are excessive in terms of cost and complexity for cases where it is necessary to focus sequencing on small selected parts of the genome.

Alongside the sequencing systems on a large scale, there is in fact currently felt the need for a method for target sequencing, typically of a single isolated gene, of which it is desired to know the exact sequence of the bases and possible variants. Such a method, possibly integrated with a PCR amplification system, would prove useful in the case where (for example, during a diagnostic examination) there is identified the presence of a particular gene, of which it is necessary to know the exact sequence (variant).

BRIEF SUMMARY

According to the present disclosure, a method and a device for nucleic acid sequencing are thus provided, as defined in the annexed claims.

BRIEF DESCRIPTION OF THE SEVERAL VIEWS OF THE DRAWINGS

For a better understanding of the present disclosure, preferred embodiments thereof are now described, purely by way of non-limiting example and with reference to the attached drawings, wherein.

DETAILED DESCRIPTION

According to the present disclosure, one embodiment provides a method for sequencing a macromolecule, in particular DNA, based upon the Sanger method, and in particular including the steps of preparing a sample and sequencing reaction according to the Sanger method without carrying out an electrophoresis step.

The Sanger method is per se known and thus is not described in detail herein, but a possible embodiment thereof is provided by way of example. The steps of preparation of the sample and of sequencing reaction require a single-strand DNA template (or template strand), a primer for starting the polymerization reaction, a DNA polymerase, and deoxynucleotides and dideoxynucleotides for terminating the polymerization reaction. The modified nucleotides (ddNTPs) or the primer, according to the present disclosure, do not have to be marked (either by radioactivity or by fluorescence) in so far as electrophoresis is not carried out. The DNA sample to be sequenced is divided into four separate reactions, each of which contains the DNA polymerase and all four deoxyribonucleotides (dATP, dCTP, dGTP, and dTTP). This step may be carried out in a test tube, or else in dedicated wells provided in an integrated chip, for example of semiconductor material. Then added to each of these reactions is just one of the four dideoxynucleotides (ddATP, ddCTP, ddGTP, and ddTTP) in stoichiometrically lower amount in order to enable a lengthening of the strand sufficient for carrying out analysis. Incorporation of a dideoxynucleotide along the growing DNA strand causes termination thereof before the end of the template DNA sequence is reached. This gives rise to a series of DNA fragments of different length interrupted by incorporation of the dideoxynucleotide, which occurs randomly when it is used by the polymerase instead of a deoxynucleotide.

Figure 1:
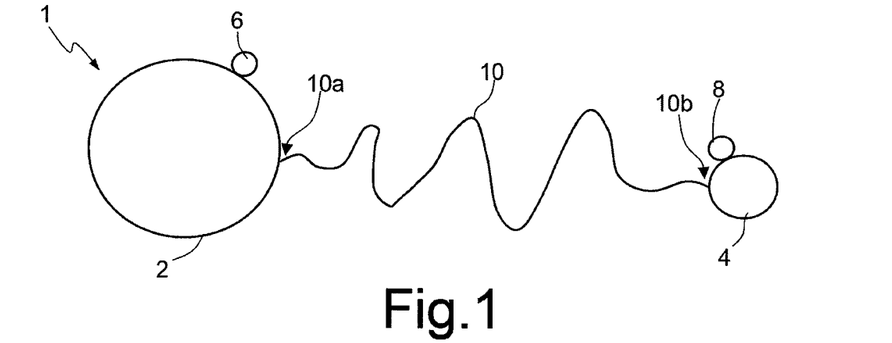
FIG. 1 illustrates a system formed by a single DNA strand coupled to functionalized masses, according to an aspect of the present disclosure.

Next, the strands thus synthesized are denatured to obtain separation of individual DNA strands from the template strands. A plurality of partial strands, or DNA fragments, is thus obtained. FIG. 1 represents one of these partial strands, designated by the reference number 10. Each partial strand typically has a length different from that of the other partial strands and terminates with a respective nucleotide base from among adenine, thymine, guanine, and cytosine.

Then, according to the present disclosure, each partial strand is assembled to form the structure 1 illustrated in FIG. 1 by binding a first end 10a of the partial strand 10 to a first mass 2, and a second end 10b of the partial strand 10 to a second mass 4. In the figures, the first and second masses 2, 4 are illustrated, for simplicity of representation, of a circular or spherical shape, without this implying that they must necessarily have this shape.

The second mass 4 is configured to bind exclusively to one of the nucleotide bases, and in particular to the base that terminates the partial strand 10 prematurely. For this purpose, four different types of second masses 4 are provided, functionalized in an appropriate way for binding each to a respective dideoxynucleotide that terminates the plurality of partial strands obtained via the aforementioned steps of the Sanger method. A first type of second mass 4 is functionalized for binding to a first dideoxynucleotide (e.g., ddATP), a second type of second mass 4 is functionalized for binding to a second dideoxynucleotide (e.g., ddTTP), a third type of second mass 4 is functionalized for binding to a third dideoxynucleotide (e.g., ddGTP), and a fourth type of second mass 4 is functionalized for binding to a fourth dideoxynucleotide (e.g., ddCTP).

The first mass 2 is configured to bind to the first end 10a of each strand 10. For this purpose, the mass may be functionalized for binding to the PCR-primer sequence.

In solution, the first mass 2 is, as a result of its dimensions and/or other characteristics (e.g., electrical characteristics and/or characteristics of hydrodynamic friction), less mobile than the second mass 4 for functioning as constraint in the oscillating movement of the DNA strand used for sequencing.

In an embodiment of the present disclosure, the first mass 2 is a protein, responding to the characteristics of the molecules referred to as "drag-tags". Drag-tag technology is already widely used and studied as method for free DNA electrophoresis in a liquid in order to determine the length of various fragments. The fundamental characteristics of the technology mentioned are briefly outlined in what follows.

It should be noted that the mobility of DNA, once a certain critical length of the strand has been exceeded, no longer depends upon the length itself, in so far as the ratio between the electrostatic pulling force (which depends linearly upon the charge at constant density, and thus upon the length of the strand) and the force of hydrodynamic friction (which also depends linearly upon the length of the strand) is constant. By attaching the strand with a molecule with a high coefficient of hydrodynamic friction (i.e., the drag-tag), the friction itself depends above all upon said additional molecule, whereas the pulling force continues to depend upon the length of the strand. In this way, there has been shown separation by electrophoresis in a liquid of DNA strands of different lengths (within a range that depends upon the characteristics of hydrodynamic friction of the drag-tag).

In contrast to the drag-tag technology in the prior art, the present disclosure is principally based on a movement of folding of the DNA strand 10 up to provide mutual contact of the two ends 10a, 10b of the DNA strand (the drag-tag is bound to one of the two ends), and consequent emission of fluorescence. In order to obtain the desired effect, it is expedient for the force that guides the oscillatory movement to be tuned in frequency and/or amplitude with the length of the DNA strand to obtain a resonance condition. This enables convenient and precise measurement of the partial lengths, improving the results that may be obtained with electrophoresis in a liquid according to the known art. Use of drag-tags (including protein drag-tags) in order to increase the overall hydrodynamic friction is performed, per se, according to the prior art, and thus this aspect is not discussed any further herein.

By way of example, see the paper by R. J. Meagher et al., "Sequencing of DNA by Free-Solution Capillary Electrophoresis Using a Genetically Engineered Protein Polymer Drag-Tag", Anal. Chem. 2008, 80, pp. 2842-2848.

See further the paper by R. D. Haynes et al., Bioconjugate Chem. 2005, 16, pp. 929-938.

Further, see the paper by Jong-In Won et al., "Protein polymer drag-tags for DNA separations by end-labeled free-solution electrophoresis", Electrophoresis 2005, 26, pp. 2138-2148.

In an embodiment of the present disclosure, the first mass 2 and the second mass 4 are both proteins of the same type as those used for drag-tags. However, whereas the mass 2 has a drag-tag function proper (i.e., contributing to increasing the overall hydrodynamic friction), the mass 4 preferably exhibits an overall net charge that renders it sensitive to the action of an applied electrical field, as illustrated more fully in what follows. Since the electrical field is not localized but acts also on the DNA strand 10, which in turn presents a non-zero electrical charge, it is preferable for the charge of the mass 4 to be much higher than the total charge of the strand 10 in order for the movement of the strand 10 itself to be guided by its end. In some embodiments, strand 10 has a maximum length of between 100 and 200 bases. Considering an elementary charge $e^-$ per base, the net charge of the mass 4 is higher (indicatively by one order of magnitude) than approximately 100e⁻ (e.g., it is approximately 1000e⁻). The charge is preferably negative to prevent attraction to the DNA strand 10, with consequent folding on the mass 2 itself.

The mass 4 is bound to the PCR primer, whereas the mass 2 is bound to the four modified bases. The techniques for functionalizing the primer and the bases, including modified ones, with other molecules are known in the prior art and thus not described in detail herein.

The first mass 2 is further functionalized with a donor molecule 6, whereas the second mass 4 is functionalized with an acceptor molecule 8. The donor molecule 6 and the acceptor molecule 8 are chosen so that, when they are brought at a distance from one another shorter than a minimum distance, there is a transfer of energy from the donor molecule 6 to the acceptor molecule 8, resulting in emission of light.

Donor and acceptor molecules that may be used include 3'-fluorescein and 5'-LC Red 640, respectively.

In the condition of FIG. 1, when the first and second masses 2, 4 are at a distance from one another and the partial strand 10 is splayed out completely or in part, there is no transfer of energy from the donor molecule 6 to the acceptor molecule 8. On the other hand, in conditions where the first mass 2 and the second mass 4 are apart from one another at a distance shorter than the minimum distance, energy transfer occurs, which cause emission of light that may be detected. See e.g., FIG. 4C. In one embodiment, the donor molecule 6 and the acceptor molecule 8 are chosen so that said minimum distance is less than a few nanometers, preferably less than 1 nm.

According to an aspect of the present disclosure, the structure 1 of FIG. 1 is subjected to a variable electrical field (e.g., sinusoidal) in order to vary in a controlled way the distance between the first and second masses 2, 4. The electrical field applied acts on the first and second masses 2, 4 and, as a result of the difference in size, and/or weight, and/or hydrodynamic friction between the two masses 2, 4, generates a relative movement of the second mass 4 with respect to the first mass 2.

Preferably, in an initial step of the method, a DC component is applied to generate a force that causes the first mass 2 to pull away from the second mass 4, thus stretching the strand 10. Said DC component may further cause a movement in space of the entire system 1, i.e., of both the masses 2, 4 and the strand 10, in an undesired way. For this purpose, it is advisable to reverse periodically the direction of the DC field for generating a substantially zero net displacement of the system 1. The DC electrical field may, for this purpose, be a signal that assumes periodically values K, 0, −K, 0, etc., where |K| is a value greater than zero. In one embodiment, the periods of high or low signal "K" have the same temporal duration, as the periods of zero signal "0". The average is a zero signal. It is possible to use, for example, a square-wave signal with zero average.

Figure 2:
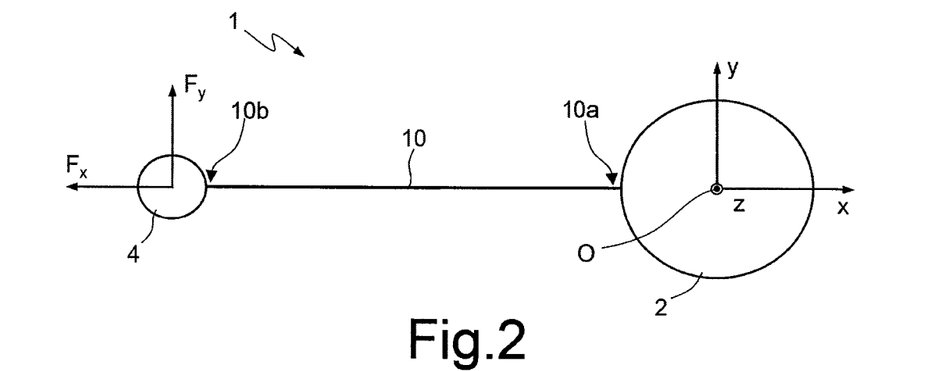
FIG. 2 illustrates the system of FIG. 1 in a reference system centered on one of the two masses and with forces acting on the other of the two masses.

With reference to the model represented schematically in FIG. 2, a system of co-ordinates X, Y, and Z is considered having origin O at the center of mass of the first mass 2.

After the DC electrical field has been applied and the DNA strand 10 has been splayed out, the DC field is turned off, and an AC electrical field is applied having a first component $F_X$ along the direction X and a second component $F_Y$ along the direction Y orthogonal to the direction X. A force component oriented along a third direction Z, orthogonal to X and Y, may be of zero value, thus allowing the second mass 4 to move along Z with Brownian motion.

Brownian motion along Z is a motion with zero average and thus does not represent a net component of movement of the system as a whole.

The component $F_X$ and the component $F_Y$ are, in this example, quadrature sinusoidal signals with a frequency ratio equal to 2 or a multiple of 2, and specifically $$F_X = A \cdot \cos(\omega t)$$

$$F_Y = B \cdot \sin(M\omega t)$$

where: A and B are the respective values of signal amplitude and are, for example, chosen with a value comprised between −10 pN and +10 pN (the sign depends upon the direction of the force); ω is the angular frequency (equal to 2πf, where f is the frequency, for example ranging between 100 MHz and 3 GHz); M is the ratio, chosen, as has been said, equal to 2 or a multiple of 2; and t is the time variable, measured in seconds.

For a nucleic acid strand of 40 bases, it has been found that a frequency of approximately 1 GHz yields good results, with an estimated sensitivity (frequency variation) of approximately 75 MHz per base.

However, it is possible to scale, also by several orders of magnitude, the frequencies and the forces, in a way that is interdependent and, in turn, depends upon the overall charge of the mass 4.

In the condition of FIG. 2, the value of amplitude B is greater than zero, whereas the value of amplitude A is smaller than zero in so far as, at a first instant of time, the force $F_X$ is applied along the negative direction of the axis X. The present applicant has in fact found that application of a positive force $F_X$, at an instant immediately subsequent to the step of stretching of the strand 10 by the DC field, may cause the strand 10 to break.

Figure 3:
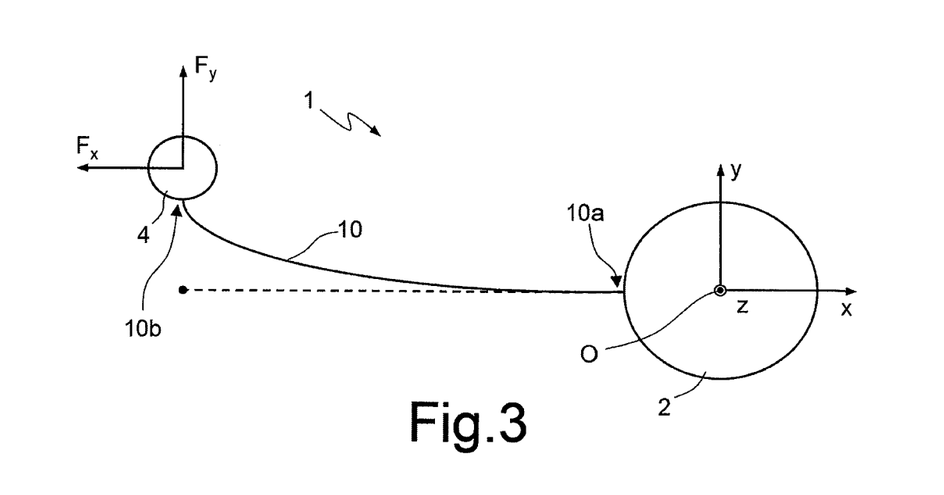
FIG. 3 illustrates the system of FIG. 2 in an operating condition of relative movement of the two masses.

With reference to FIG. 3, the force $F_X$ counters an elastic force $F_{el}$ proper to the strand 10, which tends to cause the strand 10 to roll up in order to reach a condition of maximum entropy, whereas the force $F_Y$ generates a movement that displaces the second mass 4 along a semi-curvilinear path around the first mass 2, imparting on the second mass 4 an oscillatory motion that displaces the strand 10 from the original position (represented in FIG. 3 by a dashed line).

With reference to FIGS. 4A-4E, illustrated graphically therein is the effect of application of the AC electrical field that generates the force $F_X$ and the force $F_Y$.

At time $t=t_0$ (FIG. 4A), the strand 10 is assumed as being completely splayed out, as a result of the component of DC field applied at an immediately previous instant. The force $F_X$ has, in $t=t_0$, a maximum value, i.e., equal to |A|, and a direction such as to move the first and second masses 2, 4 away from one another (e.g., $F_X = -10$ pN).

Figure 4A:
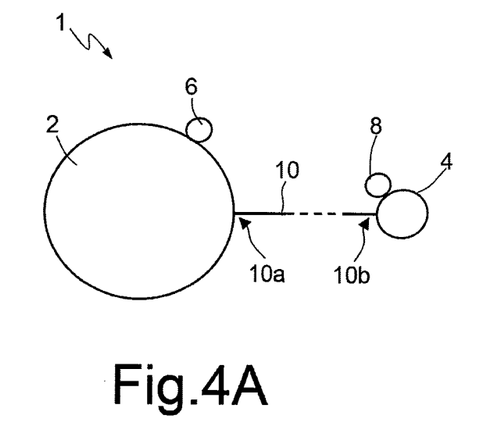
FIGS. 4A-4E illustrate steps of a control method of the system of FIG. 1, according to an aspect of the present disclosure.
Figure 4B:
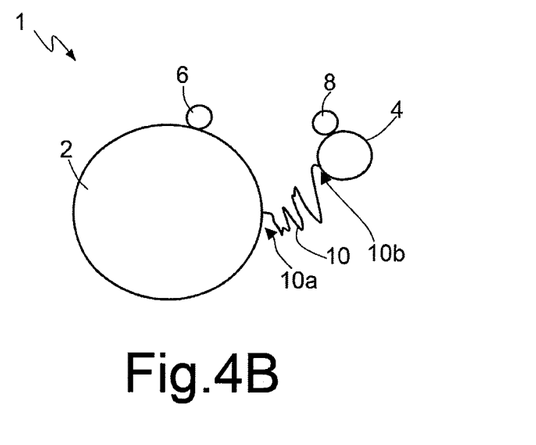

The first mass 2 is illustrated coupled to a donor molecule 6 and the second mass 3 is illustrated coupled to an acceptor molecule 8.

Then (FIG. 4B), the force $F_X$ decreases according to a sinusoidal pattern until it reaches a zero value (point of change of sign of the force $F_X$). In this situation, the strand 10 undergoes first the action of the elastic force $F_{el}$, and then the action of the force $F_X$, which favor an "arching" of the strand 10, thus bringing the first and second masses 2, 4 closer to one another.

Figure 4C:
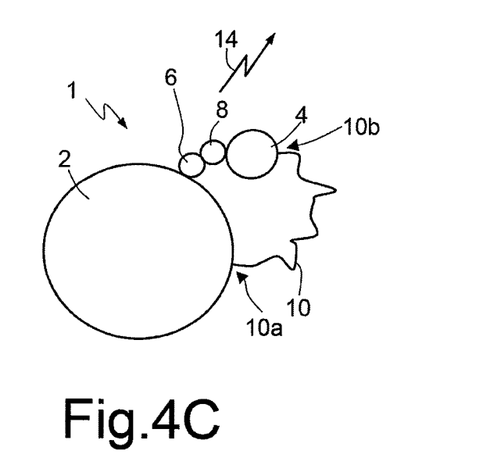

Next (FIG. 4C), the force $F_X$ increases progressively its value until the maximum value |A| is reached and with a direction such as to bring the first and second masses 2, 4 closer to one another (e.g., $F_X = -10$ pN). The force $F_Y$ generates an oscillatory movement of the second mass 4 around the first mass 2, which causes the donor molecule 6 and the acceptor molecule 8 to approach each other. In the condition of FIG. 4C, the donor molecule 6 and the acceptor molecule 8 are at a distance from one another such as to cause emission of light radiation.

In this context, it is emphasized that the condition of approach between the donor molecule 6 and the acceptor molecule 8 such as to enable emission of light radiation is a function of the parameters of length of the strand 10 and of frequency of the electrical field applied.

In particular, light emission occurs if the frequency and amplitude of the electrical field applied are "tuned" with the length of the strand 10 (a condition that is further referred to as "resonance") for enabling contact between the two masses 2 and 4, and thus between the donor molecule and the acceptor molecule; otherwise, there will not be light emission. As used herein, "tuned" frequency and amplitude refers to values that cause the semicircular movement of the strand to terminate with the donor molecule 6 and acceptor molecule 8 in contact, i.e., at a distance such as to enable energy exchange to occur, with light emission. In the case where the semicircular movement terminates at a greater distance (i.e., with reference to the Cartesian system of co-ordinates of FIG. 2, in the case where the mass 4 again assumes the co-ordinate y that is substantially 0 but, simultaneously, the co-ordinate x that is other than 0 for an amount greater than the effective radius of the mass 2, and with any sign) exchange between the donor molecule 6 and the acceptor molecule 8, and thus light emission, do not occur. In this case, the parameters are not "tuned". The values to be set for the amplitude and frequency for them to be considered "tuned" depend upon the length of the strand considered. Based on this is, in effect, the capacity of distinguishing between different lengths and, in practice, of determining the sequence in question.

The effective length of the strand 10 is not known beforehand, and consequently also the frequency (f) to be applied for reaching the condition of light emission is not known beforehand. However, by frequency sweeping in the range of frequencies already identified previously, it is possible to bring in tuned or resonance conditions, in sequence, systems 1 having strands of various lengths. The interest, in analyses of this type, is not in fact to know the absolute length of the strand 10, but to acquire information useful for sequencing the strand 10, and determining the relative lengths of strands 10 with different terminations.

An estimate of the typical lengths may be obtained from the knowledge of the length of the gene amplified by the initial PCR step and from the length of possible stretches of probe that could be used for binding the masses together. On the basis of one or both of these data, it is possible to obtain beforehand a frequency range to be applied for movement of the mass 4.

Figure 5:
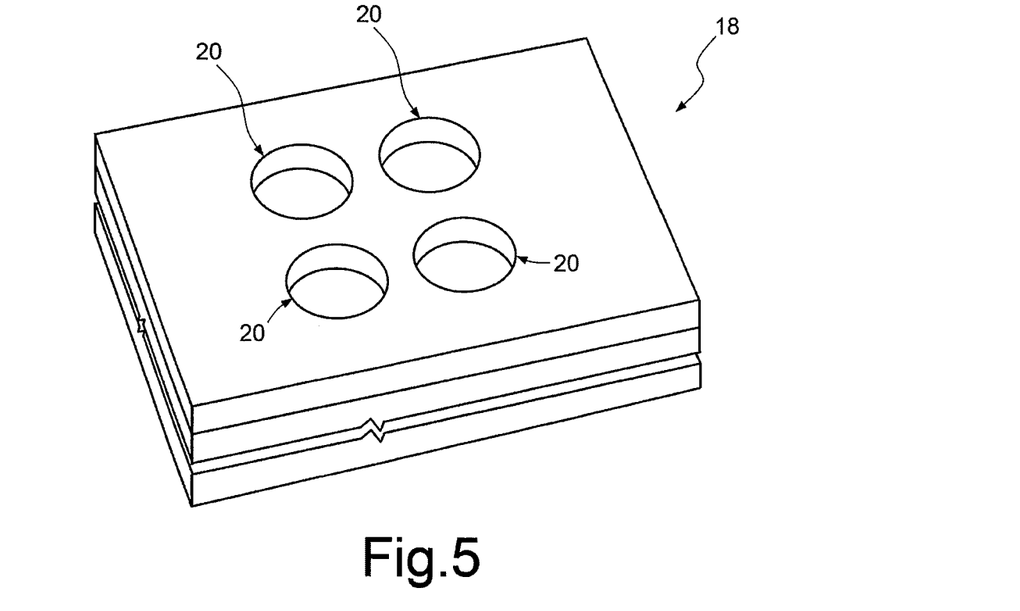
FIG. 5 illustrates a device designed to implement the method of FIGS. 4A-4E.

FIG. 5 illustrates a portion of a device 18, obtained in MEMS technology, comprising four wells 20, each of which is configured to contain a liquid solution including a plurality of structures 1 of the type described previously. The structures 1 in each well 20 include respective strands 10. The second masses 4 in a same well 20 are functionalized to be able to couple to a same type of dideoxynucleotide (the same from among ddATP, ddTTP, ddGTP, and ddCTP). Second masses 4 in different wells are functionalized to be able to couple with dideoxynucleotides of types different from one another. It follows that, carrying out the frequency sweep on the four wells 20 of the device of FIG. 5, for each value of resonance frequency (which corresponds to a specific length of the strand 10) there will be prevalent light emission from just one of said wells 20. Said light emission may thus be uniquely associated to one and only one dideoxynucleotide (one from among ddATP, ddTTP, ddGTP, and ddCTP) and, thus, to one and only one nucleotide base (a corresponding one from among A, T, G, and C).

The present applicant has estimated that the resonance frequency decreases by approximately 75 MHz for each nucleotide base (assuming a frequency range of the order of gigahertz or fractions of a gigahertz, without prejudice to the aforementioned scalability of the quantities). This means that, for example, if a strand with a length of 40 bases resonates at 1 GHz, a strand with a length of 41 bases resonates at a frequency (f) of the AC field applied of approximately 1 GHz−75 MHz (i.e., 925 MHz), whereas a strand with a length of 39 bases resonates at a frequency f of the AC field applied of approximately 1 GHz+75 MHz. It is in any case evident that the values provided above represent an embodiment and have been verified via simulations for strands with lengths comprised between 20 and 40 bases.

In general, noting that to given frequency values there is light emission corresponding to a specific nucleotide base and knowing that, by increasing the length of the strand 10, the resonance frequency decreases, it is possible to carry out a frequency sweep starting from a maximum frequency value and reduce said value either by predefined steps (for example, by steps of 20-50 MHz to be on the safe side) or continuously. By observing the sequence of "lighting" of the wells 20, the sequence of the bases that form the strand 10 under analysis is consequently acquired.

Figure 4D:
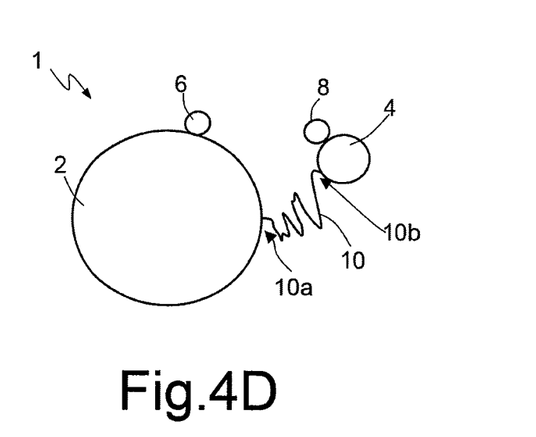
Figure 4E:
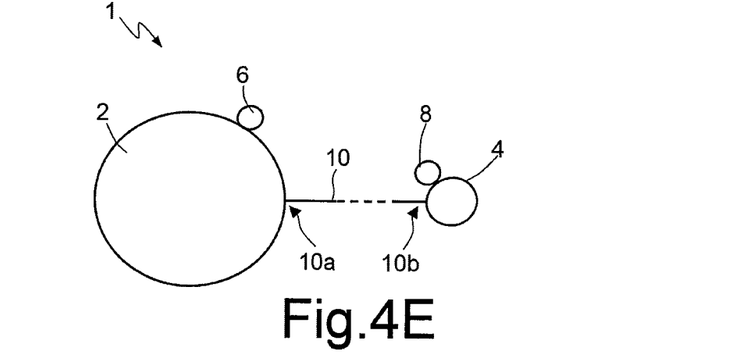

Finally, with reference to FIG. 4D, by bringing, following a sinusoidal pattern, the value of the force $F_X$ back to negative values (−10 pN according to the previous example), there is caused a progressive recession of the second mass 4 from the first mass 2, and the system 1 is brought back to the condition of FIG. 4A (time t=0).

The steps of FIGS. 4A-4E are carried out a plurality of times, continuously, for each frequency value (for example, maintaining a given frequency value for some microseconds, or some tens of microseconds). The cycle continues, as illustrated previously, by varying the value of frequency of the sinusoidal electrical field up to completion of sequencing.

Figure 6:
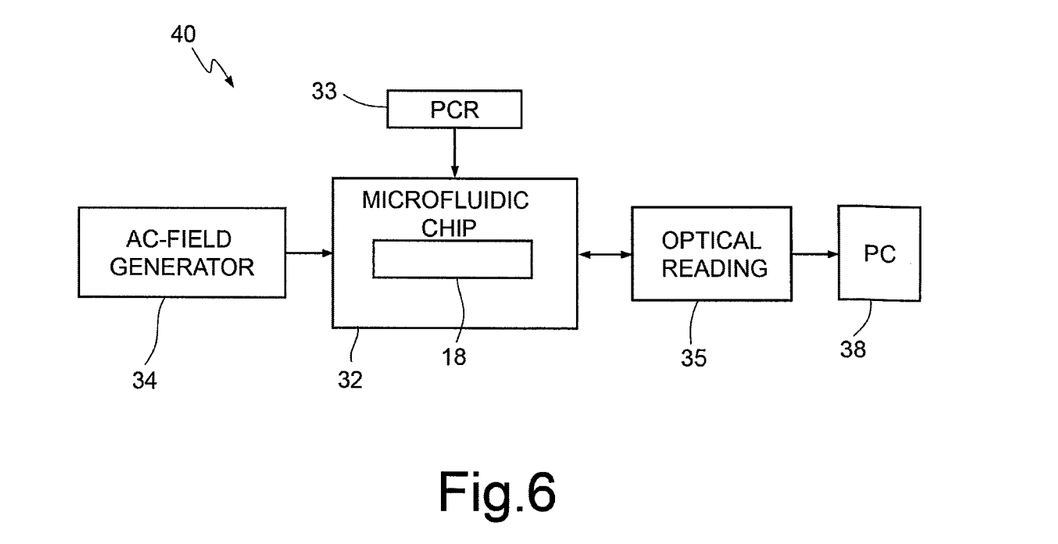
FIG. 6 illustrates the block diagram of a system for DNA amplification and sequencing, according to an aspect of the present disclosure.

FIG. 6 is a schematic illustration of a microfluidic system 40 according to one aspect of the present disclosure. The microfluidic system 40 comprises a microfluidic chip 32, including the device 18 of FIG. 5, and optionally reserves of reagents for implementation of the Sanger method, according to embodiments of the present disclosure.

A PCR chip 33 has the function of carrying out amplification of the DNA segments, according to the protocol envisaged by PCR, and introducing the amplified segments into the microfluidic chip 32, for carrying out the protocol of a Sanger type.

A generator of DC/AC electrical field 34 is operatively coupled to the device 18 for generation of the fields previously described, in particular for generation of the forces $F_X$ and $F_Y$.

Finally, an optical reading unit 35 is operatively coupled to the device 18 for optical reading of the signal of light radiation emitted during the use, as described previously.

The light information acquired by the optical reading unit 35 may be sent, for an automatic analysis or an analysis assisted by an operator, to processing means, for example a computer (PC), 38.

Advantageously, the present disclosure provides a simple and low-cost system for target sequencing of DNA subsequences of interest. The method described may be integrated with possible PCR steps already present in chips of a known type for carrying out a single analysis (in particular, in an automatic way) of the possible sequence identified by the PCR. The method according to the present disclosure is further simpler and economically advantageous as compared to global sequencing techniques of a known type.

Finally, it is clear that modifications and variations may be made to what has been described and illustrated herein, without thereby departing from the scope of the present disclosure, as defined in the annexed claims.

For example, it is possible to implement the method described in a microfluidic device provided with a single well, unlike what is shown in FIG. 5. In this case, each donor-acceptor pair is configured to emit light radiation of a different color as a function of the dideoxynucleotide (ddATP, ddTTP, ddGTP, ddCTP) to which the mass 4 is coupled. In this way, the sequence of the colors indicates the type of base sought for sequencing.

Further, according to a further embodiment, the AC field along X and along Y may be generated using a signal other than a sinusoid, for example an AC signal such as a square wave.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device for sequencing a nucleic acid strand, comprising:
   a plurality of wells, wherein each well houses:
      a solution containing truncated strands extending between a respective first end and a respective second end and having lengths different from one another, wherein the second end terminates with a respective dideoxynucleotide from among ddATP, ddTTP, ddGTP, and ddCTP;
      first masses, coupled to the first end of each truncated strand, and functionalized with a donor molecule;
      second masses, functionalized for binding only to a respective terminal dideoxynucleotide of the second end of each strand, and functionalized with an acceptor molecule,
      wherein the donor molecule and the acceptor molecule are configured to emit light radiation when the donor module is spaced a distance from the acceptor molecule, the distance being shorter than a minimum distance;
   an electrical-field generator configured to generate an AC electrical field having a frequency and an amplitude to impress, on each second mass, a net movement directed towards the first mass to which each of the second masses is coupled via said truncated strand;
   control means for controlling the electrical-field generator, configured to vary the frequency value in a predefined frequency range;
   reading means, configured to acquire a plurality of light radiations emitted by each well at respective frequency values in said range; and
   analysis means, configured to associate each light radiation acquired to a respective dideoxynucleotide and, thus, to a respective nucleotide base.

2. The device according to claim 1, wherein the second mass is functionalized to create a unique association between the color of the light radiation emitted by a respective second mass and the respective dideoxynucleotide to which the second mass is bound so that the color of said light radiation emitted uniquely identifies a single dideoxynucleotide from among ddATP, ddTTP, ddGTP, and ddCTP.

3. The device according to claim 1, wherein the means for control of the electrical-field generator are further configured to govern generation of an electrical field having a frequency and an amplitude to cause, on each second mass, a first force ($F_X$) oriented along a first direction (X) and a second force ($F_Y$) oriented along a second direction (Y), wherein the first direction corresponds to the direction parallel to the truncated strand in a condition of maximum extension thereof, and the second direction is orthogonal to the first direction.

4. The device according to claim 3, wherein the means for control of the electrical-field generator are further configured to govern generation of a DC electrical field to generate, on each second mass, a force that causes recession of the second mass from the first mass, bringing about said maximum extension of the truncated strand in said first direction.

5. The device according to claim 1, wherein the first mass is a molecule with a higher coefficient of hydrodynamic friction than a molecule of the second mass.

6. The device according to claim 1, wherein the first mass is a protein of a drag-tag type configured to increase a coefficient of hydrodynamic friction of the first mass.

7. The device according to claim 3, wherein the second mass has a net charge such that it is guided along the first and second directions under the action of the AC electrical field.

8. The device according to claim 1, wherein the first mass is functionalized with said donor molecule, and the second mass is functionalized with said acceptor molecule, said minimum distance being less than 1 nm.

9. The device according to claim 3, wherein the first force ($F_X$) and the second force ($F_Y$) are generated by quadrature sinusoidal signals with a frequency ratio equal to 2 or a multiple of 2, such that $F_X = A \cdot \cos(\omega t)$ and $F_Y = B \cdot \sin(2\omega t)$, where A and B are the respective values of signal amplitude, $\omega$ is the angular frequency, and t is the time variable.

10. The device according to claim 9, wherein the first force ($F_X$) and the second force ($F_Y$) co-operate for generating a movement that displaces the second mass along a semi-curvilinear path around the first mass, imparting upon the second mass an oscillatory motion.

11. The device according to claim 1, wherein the means for control of the electrical-field generator are further configured to vary the frequency value in a predefined frequency range making a frequency sweep in said predefined frequency range for generating resonance conditions that are specific for different lengths of the truncated strands.

12. The device according to claim 1, comprising a microfluidic chip that houses in an integrated form: said wells; one or more reserves of reagents for formation of said truncated strands, which is fluidically coupled to the wells; and one or more chambers for carrying out a PCR, which is fluidically coupled to the wells and/or to said one or more reserves of reagents.

13. A device for sequencing nucleic acid strands, comprising:
a plurality of wells containing aliquots of nucleic acid strands, one terminus of each nucleic acid strand being terminated by a respective dideoxynucleotide selected from the group consisting of ddATP, ddTTP, ddGTP, and ddCTP, and each nucleic acid strand, at respective terminus, being functionalized with an energy donor and an energy acceptor capable of emitting light radiation when arranged at a distance below a minimum distance;
an electrical-field generator configured to generate an AC electrical field of a frequency and amplitude in each well;
a control device for controlling the electrical-field generator, configured to vary the frequency value in a predefined frequency range; and
a reading device configured to acquire a plurality of light radiations emitted from each well at respective frequency values in said range.

14. The device according to claim 13, further comprising an analysis device configured to associate each light radiation acquired to a respective dideoxynucleotide and a respective nucleotide base.

15. The device according to claim 13, wherein the control device is further configured to govern generation of an electrical field having a frequency and an amplitude to cause a first force ($F_X$) oriented along a first direction (X) and a second force ($F_Y$) oriented along a second direction (Y), wherein the first direction is parallel to the nucleic acid strand in a condition of maximum extension thereof, and the second direction is orthogonal to the first direction.

16. The device according to claim 15, wherein the first force ($F_X$) and the second force ($F_Y$) are generated by quadrature sinusoidal signals with a frequency ratio equal to 2 or a multiple of 2 such that $F_X = A \cdot \cos(\omega t)$ and $F_Y = B \cdot \sin(2\omega t)$, where A and B are the respective values of signal amplitude, $\omega$ is the angular frequency, and t is the time variable.

17. A device for sequencing a nucleic acid strand, comprising:
a well including a solution containing a plurality of nucleic acid strands of different lengths, wherein each nucleic acid strand of a first set of the plurality of nucleic acid strands has opposite ends coupled to a first donor molecule and a first acceptor molecule, respectively, each nucleic acid strand of a second set of the plurality of nucleic acid strands has opposite ends coupled to a second donor molecule and a second acceptor molecule, respectively, each nucleic acid strand of a third set of the plurality of nucleic acid strands has opposite ends coupled to a third donor molecule and a third acceptor molecule, respectively, and each nucleic acid strand of a fourth set of the plurality of nucleic acid strands has opposite ends coupled to a fourth donor molecule and a fourth acceptor molecule, respectively, wherein each pair of the first donor molecule and the first acceptor molecule, the second donor molecule and the second acceptor molecule, the third donor molecule and the third acceptor molecule, and the fourth donor molecule and the fourth acceptor molecule is configured to emit a light radiation of a particular color associated with a corresponding dideoxynucleotide from among ddATP, ddTTP, ddGTP, and ddCTP when arranged at a distance below a corresponding minimum distance; and
an electrical-field generator adapted to generate an electrical field with a frequency range, wherein distances between each pair of the first donor molecule and the first acceptor molecule, the second donor molecule and the second acceptor molecule, the third donor molecule and the third acceptor molecule, and the fourth donor molecule and fourth acceptor molecule are changed in response to changes of frequencies in the frequency range.

18. The device of claim 17, wherein one end of each nucleic acid strand of the plurality of nucleic acids is coupled to a corresponding first mass, wherein each of the first donor molecule, the second donor molecule, the third donor molecule, and the fourth donor molecule is coupled to a corresponding first mass.

19. The device of claim 18, wherein another end of each nucleic acid strand of the plurality of nucleic acids is coupled to a corresponding second mass, wherein the another end of each nucleic acid strand of the first set is terminated with ddATP, the another end of each nucleic acid strand of the second set is terminated with ddTTP, the another end of each nucleic acid strand of the third set is terminated with ddGTP, and the another end of each nucleic acid strand of the fourth set is terminated with ddCTP, and wherein each of the first acceptor molecule, the second acceptor molecule, the third acceptor molecule, and the fourth acceptor molecule is coupled to a corresponding second mass.

20. The device of claim 17, further comprising an analysis device configured to associate each light radiation to a respective dideoxynucleotide associated with a respective nucleotide base.

* * * * *

UNITED STATES PATENT AND TRADEMARK OFFICE
CERTIFICATE OF CORRECTION

PATENT NO.        : 10,597,716 B2
APPLICATION NO.   : 15/394371
DATED             : March 24, 2020
INVENTOR(S)       : Alessandro Paolo Bramanti and Marco Angelo Bianchessi It is certified that error appears in the above-identified patent and that said Letters Patent is hereby corrected as shown below:

On the Title Page

"OTHER PUBLICATIONS", Line 3:
"DNA by by" should read -- DNA by --.

In the Claims

Column 11, Line 39, in Claim 16:
"2such" should read -- 2, such --.

Signed and Sealed this
Ninth Day of June, 2020

Andrei Iancu
*Director of the United States Patent and Trademark Office*